United States Patent [19]

Signorini

[11] Patent Number: 4,986,428

[45] Date of Patent: Jan. 22, 1991

[54] DISPOSABLE NURSER

[76] Inventor: Alberto Signorini, Rua Engenheiro Alvaro Niemeyer, 113, Sao, Rio de Janeiro, Brazil

[21] Appl. No.: 470,576

[22] Filed: Jan. 26, 1990

Related U.S. Application Data

[63] Continuation-in-part of Ser. No. 345,723, Jun. 2, 1989.

[30] Foreign Application Priority Data

Jun. 8, 1988 [BR] Brazil .................................. 8802780

[51] Int. Cl.$^5$ ............................. A61J 9/00; A61J 9/08
[52] U.S. Cl. ..................................... 215/11.3; 215/11.6
[58] Field of Search ............................... 215/11.1–11.6

[56] References Cited

U.S. PATENT DOCUMENTS

| | | | |
|---|---|---|---|
| 2,448,569 | 9/1948 | Allen | 215/11.1 |
| 2,497,198 | 2/1950 | Allen | 215/11.1 |
| 2,508,481 | 5/1950 | Allen | 215/11.3 |
| 2,520,335 | 8/1950 | Piazze | 215/11.3 |
| 2,643,448 | 6/1953 | Piazze | 215/11.3 X |
| 2,826,324 | 3/1958 | Hoag | 215/11.3 |
| 3,161,311 | 12/1964 | Boston | 215/11.3 |
| 3,362,555 | 1/1968 | Soto | 215/11.3 |
| 3,762,542 | 10/1973 | Grimes | 215/11.3 X |
| 3,790,017 | 2/1974 | Fitzpatrick et al. | 215/11.3 |
| 4,238,040 | 12/1980 | Fitzpatrick | 215/11.3 |

FOREIGN PATENT DOCUMENTS

| | | | |
|---|---|---|---|
| 492173 | 4/1953 | Canada | 215/11.1 |
| 515466 | 8/1955 | Canada | 215/11.1 |

Primary Examiner—Sue A. Weaver
Attorney, Agent, or Firm—Pettis & McDonald

[57] ABSTRACT

A disposable nurser comprising a flexible bottle that is removably inserted within a bottle holder so that the open end of the flexible bottle is folded over the top edge and down the exterior sides of the bottle holder. A countercap comprising a sleeve is slidably mounted around the bottle holder and is slid upward from the bottom of the bottle holder, over the open ends of the flexible bottle, and upward until it engages a stop means that prevents the countercap from moving further. A nipple holding cap having a nipple inserted therein is removably attached to the countercap so that the nipple is sealingly connected in fluid flow relationship with the flexible bottle.

5 Claims, 1 Drawing Sheet

U.S. Patent
Jan. 22, 1991
4,986,428
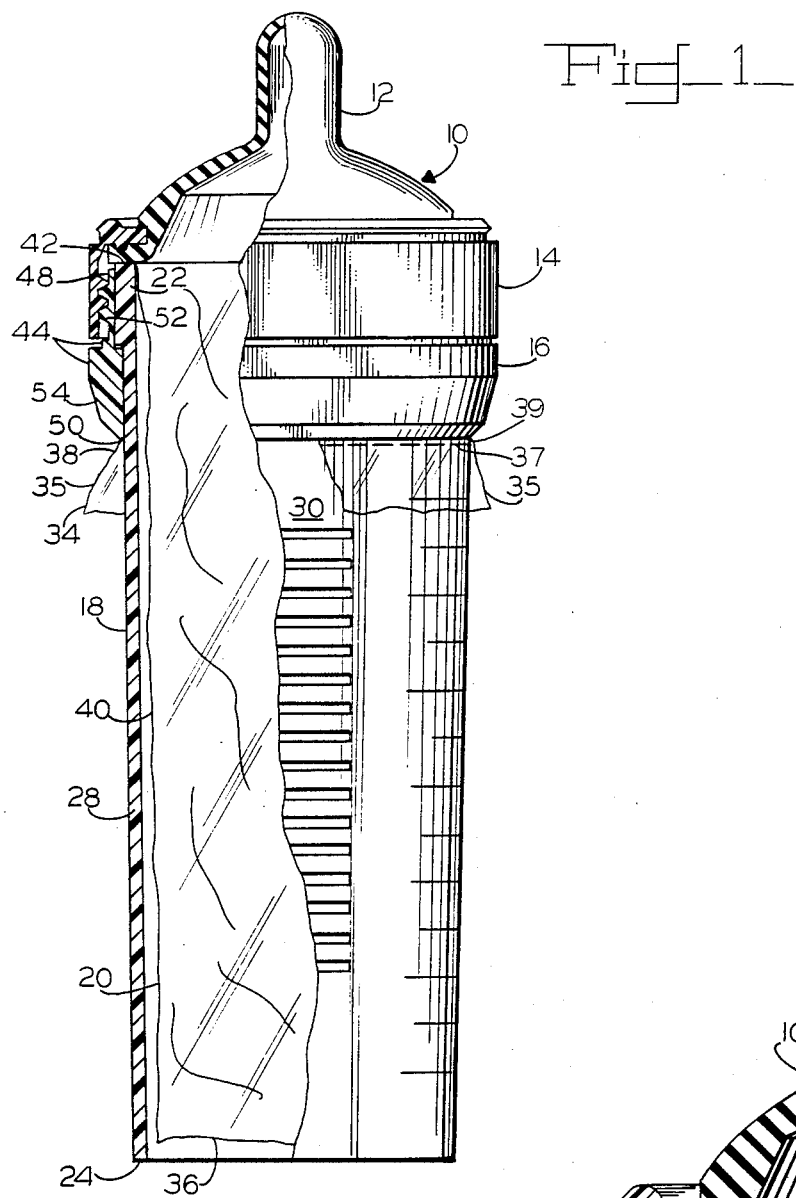
Fig_1
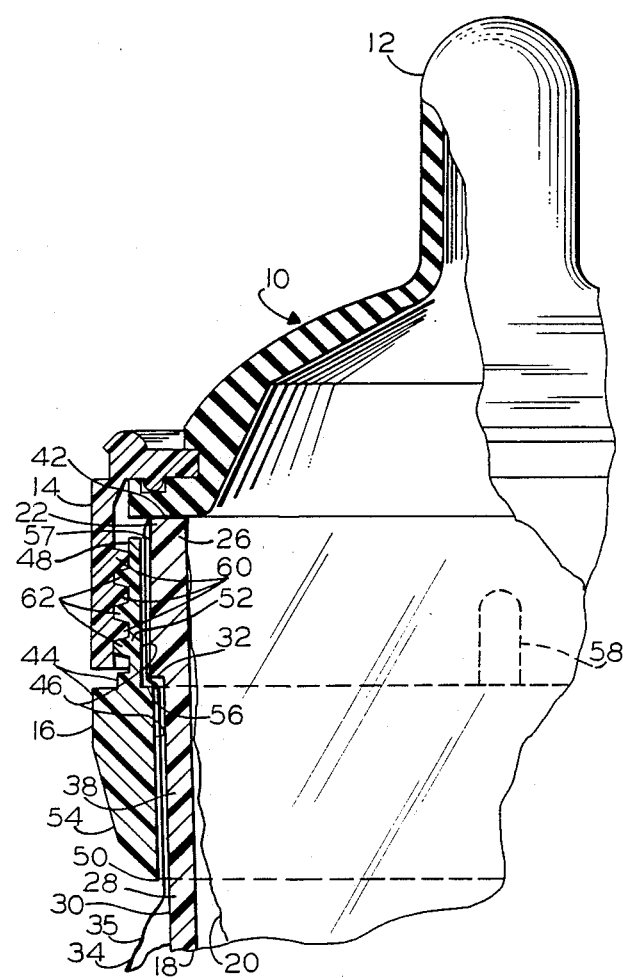
Fig_2

DISPOSABLE NURSER

RELATED APPLICATIONS

This application is a Continuation-In-Part of my pending application Ser. No. 07/345,723, filed June 2, 1989, entitled NURSING APPARATUS, which claims priority on a Brazilian application No. 8802780, filed June 8, 1988.

BACKGROUND OF THE INVENTION

1. Field of the Invention.

This invention relates to a nursing apparatus, and more particularly, to disposable nursers having flexible liners or bottles.

2. Description of the Prior Art.

The use of disposable liners, referred to in the industry as bottles, with or without separate bottle holders is well known in the industry. The major problem that most of the prior art has attempted to solve is the means by which the flexible bag is filled and then connected to a nipple ready for use.

Many disposable nursing systems attach the liner directly to a cap to which a nipple is attached. Such a system is very difficult to use, resulting in slippage of the liner causing spillage or contamination of the sterile surfaces of the liner. U.S. Pat. No. 2,508,481 issued to Adda Allen and U.S. Pat. No. 2,520,335 issued to Thomas Piazze disclose such a system.

Many disposable nursers use a bottle holder to provide support and protection for the flexible bottle. The flexible bottle is inserted within the bottle holder with the flexible bottle's open end extending beyond the upper edge of the holder, and it is then folded outward and down along the bottle holder's exterior surface. The liner must be held in place with one hand while it is being filled and capped with the other, which frequently results in slippage of the liner causing spillage or contamination of the sterile surfaces of the disposable nurser. Frequently this type of system uses a cap which is screwed to the top of the bottle holder, causing the flexible bottle to pass between the threads of the cap and the bottle holder. This often results in leakage from torn liners or an inadequate seal between the cap and the flexible bottle. In such a system, it is also difficult to add additional fluid to the bottle after it has been sealed the first time. U.S. Pat. No. 3,362,555 issued to Ricardo Soto discloses such an apparatus.

Some nursing systems do away with the threads and use a snap-on cap, or nipple, which reduces the problem caused by the threads but provides a system that is far less secure from accidental removal of the cap or nipple than a system using screw threads. Such prior art is disclosed by U.S. Pat. No. 3,790,017 issued to William Fitzpatrick, et al., and to Thomas Piazze, U.S. Pat. No. 2,643,448.

U.S. Pat. No. 3,161,311 issued to Frank Boston discloses a rubber band placed over the bottle holder which keeps the liner in place during filling and handling; however, the flexible bottle still passes between the screw threads which fasten the nipple to the bottle.

U.S. Pat. No. 3,593,871 issued to Larry Bundy discloses a nipple which has been directly sealed to a bag, with both the nipple and the bag being disposable. The bag is filled through a separate filler tube. This solves the problems discussed above but provides a very inconvenient means for filling the bottle and a more expensive system.

U.S. Pat. No. 2,599,630 issued to Emma Hair discloses a hard disposable container which may be held on a ring during the filling process, if the container is rigid enough. If the typical flexible bottle is used, it would be necessary to pass the open end of the bottle over the upper lip of this ring. This then places the liner between the threads of the ring and the nipple holding cap with all the same problems of slippage, tearing of the liner, and leakage, discussed above.

It remains clear that there is a need for a disposable nursing system which will hold the flexible bottle firmly during the filling process, would permit heating in a microwave, and provide a tight seal and secure connection between the nipple and the flexible bottle.

SUMMARY OF THE INVENTION

The present invention relates to a disposable nursing system that provides the benefits gained by the use of disposable flexible bottles and retains the benefits of the ease of handling provided by the hard nondisposable bottles. The present invention firmly clamps the flexible bottle within the bottle holder so that the bottle can be filled without fear of the flexible bottle's slipping, causing spillage and contamination. Such a system will also permit placing of the bottle within a microwave for heating without having to attach a lid to hold the flexible bottle in place. Sealing a lid to the flexible bottle could cause excessive pressure build-up and an explosion during the heating process. Most simply stated, the disposable nurser of this invention comprises a bottle holder, a countercap which is slidably mounted on the bottle holder, a nipple, and a nipple holding cap in which the nipple may be mounted.

The bottle holder is comprised of a hollow frustum that is open at both ends with one end thus having a larger circumference than the other end. A plastic liner, denominated flexible "bottle" by the industry, is inserted within the bottle holder such that the open end of the flexible bottle is pulled back over the upper lip of the larger end of the bottle holder and downward along the exterior of the bottle holder. The countercap, comprising a sleeve in which one end has a greater circumference than the other end, is so sized and configured that the large end of the sleeve may be slidably mounted over the smaller end of the bottle holder. The countercap may then be slid upward over the open end of the flexible bottle until a stop means is engaged, which prevents the countercap from advancing any further. A nipple may be removably mounted within a nipple holding cap which then may be removably attached to the larger end of the countercap, which results in the nipple's being connected to the larger end of the bottle holder and being removably sealed in liquid flow relationship with the flexible bottle.

The invention accordingly comprises an article of manufacture possessing the features, properties and the relation of elements which will be exemplified in the article hereinafter described, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which:

FIG. 1 is a front elevation, half of which is broken away to show a cross section of the disposable nurser; and FIG. 2 is a detail of the front elevation of the disposable nurser.

Similar reference characters refer to similar parts throughout the two views of the drawings.

DETAILED DESCRIPTION

A preferred embodiment of the disposable nurser is illustrated in the drawing figures. The disposable nurser is generally indicated as 10 in the views of FIGS. 1 and 2. Referring to FIGS. 1 and 2, it can be seen that the disposable nurser 10 comprises a nipple 12, a nipple holding cap 14, a countercap 16, a bottle holder 18, and a flexible bottle 20.

The bottle holder 18 is comprised of a hollow frustum having a first end 22 and a second end 24, both of the ends being open. The hollow frustum includes those frustums whose vertex is at an infinite distance from the base, which would include a generally cylindrical configuration. The preferred embodiment incorporates a hollow frustum with a finite vertex. The bottle holder 18 also has a first portion 26 and a second portion 28. The circumference of the exterior surface 30 of the bottle holder 18 is greater around the first portion 26 of the bottle holder 18 than the circumference around the second portion 28 of the bottle holder 18, defining an annular shoulder 32 interposed between the first portion 26 and the second portion 28 of the bottle holder 18.

The flexible bottle 20 has an open end 34 and a closed end 36. The flexible bottle can also be considered to have a first part 38, which includes the open end and a second part 40 which includes the closed end 36. The second part 40 of the bottle 20 is inserted within the bottle holder 18 so that the closed end 36 of the bottle 20 is proximal to the second end 24 of the bottle holder 18. The first part 38 of the flexible bottle 20 is extended beyond the first end 22 of the bottle holder 18, is then turned downward over the top edge 42 of the bottle holder 18, thus lying between the top edge 42 and the nipple 12, and then along the exterior surface 30 of the bottle holder 18. To facilitate installation of the flexible bottle 20, the open end 34 of the flexible bottle 20 may be comprised of a pair of tabs 35 which may be perforated as at 37 for easy removal later.

The countercap 16 comprises a sleeve having an exterior surface 44 and an interior surface 46, a first end 48 and a second end 50, and a first section 52 and a second section 54. The first section of the countercap 52 has an interior circumference greater than the interior circumference of the second section 54, thus defining an annular shoulder 56 interposed between the first section 52 and the second section 54 of the countercap 16. The countercap 16 is so dimensioned and configured that it may be mounted on the bottle holder 18 by inserting the second end 24 of the bottle holder 18 into the first end 48 of the countercap 16 and then sliding the countercap 16 upward toward the first end 22 of the bottle holder 18. The countercap 16 may be slid upward on the bottle holder 18 over the open end 34 of the flexible bottle 20 so that the first part 38 of the bottle 20 lies between the interior surfaces 46 of the countercap 16 and the exterior surfaces 30 of the bottle holder 18.

In the preferred embodiment, the countercap 16 and the bottle holder 18 are so configured that the annular shoulder 32 of the bottle holder 18 and the annular shoulder 56 of the countercap 16 are opposed and engage one another, creating a stop means, preventing the countercap 16 from advancing further up the bottle holder 18. When the stop means is engaged, the first end 48 of the countercap 16 reaches a stop position 57 which is located intermediate the first end 22 and the second end 24 of the bottle holder 18. It can be easily seen that the shoulder 32 of the bottle holder 18 may be located at any point intermediate the first end 22 and the second end 24 of the bottle holder 18. In the preferred embodiment, the opposing shoulders 32 and 56 are so located that the proper stop position 57 of the first end 48 of the countercap 16 is attained. In the preferred embodiment, the stop position 57 of the first end 48 of the countercap 16 is proximal to said top edge 42 of the bottle holder 18 but the first end 48 of the countercap 16 does not contact the nipple 12.

While the preferred embodiment identifies the stop means as a pair of opposing annular shoulders 32 and 56, it can be easily seen that as the bottle holder 18 comprises a hollow frustum, the exterior surface 30 may have a gradually increasing circumference and that the countercap 16 may be designed to have a similar slope to its interior surface 46. If the bottle holder 18 and the countercap 16 are so dimensioned, a friction stop will result as the countercap is slid upward on the bottle holder 18 toward the first end 22 of the bottle holder 18. It would also be a matter of design choice to use other types of interlocking protrusions on the interior surface 46 of the countercap and the exterior surface 30 of the bottle holder 18 to provide a stop means.

In FIG. 2, a protrusion 58 is shown located on the interior surface 46 of the first section 52 of the countercap 18. This protrusion 58 in the preferred embodiment is shown as a ridge type structure but may take any number of different configurations, including, but not necessarily limited to, nubs, a series of ridges, and so forth. In the preferred embodiment, three of these protrusions 58 are used as a means of controlling the tightness of the fit between the first section 52 of the countercap 16 and the first portion 26 of the bottle holder 18, which permits a fit tight enough to resist downward slippage of the countercap 16 and yet permit easy intentional removal of the countercap 16.

The nipple 12 is inserted within the nipple holding cap 14. The nipple holding cap 14 may then be removably attached to the countercap 16 by an attaching means which may be any of those means well known in the art. In the preferred embodiment, nipple holding cap 14 has a set of screw threads 60 formed on its interior surface, and screw threads 62 are formed about the exterior surface 44 of the countercap 16 proximal to the first end 48 of the countercap 16. The screw threads 60 of the nipple holding cap 14 may be removably engaged with the screw threads 62 of the countercap 16 causing the nipple 12 to be sealingly connected to the top edge 42 of the bottle holder 18. Since the flexible bottle 20 passes over the top edge 42 of the bottle holder 18, the flexible bottle 20 is therefore squeezed between nipple 12 and top edge 42 of the bottle holder 18, causing the flexible bottle 20 to be sealingly connected to the nipple and in fluid flow connection. The nipple 12 and the nipple holding cap 14 are further shown and described in my co-pending application Ser. No. 07/345,723 which was filed on June 2, 1989, which description is incorporated herein by reference. In the preferred embodiment, all the parts, with the exception of the nipple, which is constructed of latex rubber, are formed of plastic material. However, the disposable nurser may be made from any suitable materials.

Having thus set forth a preferred construction for the disposable nurser 10 of this invention, it is to be remembered that this is but a preferred embodiment. Attention is now invited to a description of the use of the disposable nurser 10.

The parts of the disposable nurser 10 are disassembled and cleaned prior to the next use with the nipple 12 generally being the only part requiring sterilization. A sterile flexible bottle is inserted within the bottle holder 18 so that the closed end 36 of the flexible bottle is proximal to the second end 24 of the bottle holder. The open end 34 of the flexible bottle 20 is separated and pulled downward by its tabs 35 over the top edge 42 of the bottle holder 18 and downward along the exterior surface 30 of the bottle holder 18. The countercap 16 is mounted over the second end 24 of the bottle holder 18 and slid upward along the bottle holder 18 passing over the first part 38 of the bottle 20 such that the open end 34 of the bottle 20 extends downward below the second end 50 of the countercap 16.

The countercap 16 is pushed to the stop position 57 such that the annular shoulder 32 of the bottle holder 18 and the opposing annular shoulder 56 of the countercap 16 are engaged and the first part 38 of the bottle 20 is pinched and held between the opposing shoulders. With the countercap 16 in the stop position, the protruding ridge 58 provides a friction fit between the countercap 16 and the bottle holder 18 resisting downward movement by the countercap 16.

Milk or other fluids may now be poured into the flexible bottle 20 and, if desired, the fluid may be heated in a microwave without risk of a buildup of pressure or risk of the flexible bottle 20 sliding free. When the milk or other fluid is warmed, the nipple 12 is placed within the nipple holding cap 14, which is then removably attached to the countercap 16. By tightly screwing the nipple holding cap 14 onto the countercap 16, the nipple 12 is sealingly attached to the flexible bottle 20 and a fluid flow relationship will exist between the nipple 12 and the flexible bottle 20. At this time, the tabs 35 may be removed along their perforations 37 so that the first part 38 of the bottle 20 now ends 39 at a point generally adjacent to the second end 50 of the countercap 16. The disposable nurser 10 is now ready for use.

It will thus be seen that the objects set forth above, among those made apparent from the preceding description, are efficiently attained and, since certain changes may be made in the above article without departing from the scope of the invention, it is intended that all matter contained in the above description, or shown in the accompanying drawings, shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A disposable nurser comprising:
   a bottle holder comprising a hollow frustum having a first portion and a second portion, having an exterior and an interior surface and having first and second ends, both said ends being open, said second end of said hollow frustum having a smaller circumference than said first end of said hollow frustum;
   a flexible bottle having an open end and a closed end and having a first part including said open end and a second part including said closed end, said second part of said flexible bottle removably inserted within said bottle holder, such that said closed end is proximal to said second end of said bottle holder and said first part of said flexible bottle extends beyond said first end of said bottle holder, over said first end of said bottle holder, and downward adjacent to said exterior surface of said bottle holder;
   a countercap comprising a sleeve having exterior and interior surfaces, having a first end and a second end, and having a first section and a second section, said sleeve so sized and configured that said first end of said sleeve may be slidably mounted over said second end of said bottle holder and said first part of said flexible bottle, such that said first part of said flexible bottle rests between said exterior surface of said bottle holder and said interior surface of said sleeve, and said sleeve may be slid to a stop position, such that said first end of said sleeve is proximal to said first end of said bottle holder;
   a stop means located at a predetermined point intermediate said first and said second ends of said bottle holder, such that when said countercap is mounted on said bottle holder, said first end of said countercap is prevented from advancing beyond said stop position;
   a nipple removably connected to said first end of said bottle holder;
   a nipple holding cap to which said nipple may be removably mounted, said cap having an interior surface; and
   an attaching means wherein said nipple holding cap may be removably attached to said countercap, such that said nipple is connected to said first end of said bottle holder and is removably sealed in liquid flow relationship to said flexible bottle.

2. A disposable nursing bottle as in claim 1 wherein said stop means comprises an annular shoulder located on said exterior surface of said bottle holder, wherein said first portion of said bottle holder has an exterior circumference greater than the exterior circumference of said second portion of said bottle holder, thus defining said annular shoulder interposed therebetween; an opposing interior annular shoulder on said interior surface of said countercap, wherein said first section of said countercap has an interior circumference greater than the interior circumference of said second section of said countercap, thus, defining said annular shoulder interposed therebetween, said bottle holder and said countercap so dimensioned that when said first end of said sleeve is slidably mounted over said second end of said bottle holder, said shoulder of said sleeve engages said opposing shoulder of said bottle holder, whereby said sleeve cannot be advanced further.

3. A disposable nursing bottle as in claim 1 wherein said attaching means for said nipple holding cap further comprises screw threads formed on said exterior surface of said countercap sleeve proximal to said first end of said sleeve, and screw threads formed on said interior surface of said nipple holding cap such that said screw threads of said nipple holding cap may be removably engaged with said screw threads of said countercap, whereby said nipple when mounted in said nipple holding cap is sealingly connected to said first end of said bottle holder.

4. A disposable nursing bottle as in claim 1 wherein said countercap further comprises at least one protruding bump projecting from said interior surface of said countercap located at a predetermined point intermediate said first end of said countercap and said second end of said countercap.

5. A disposable nurser as in claim 2 wherein said countercap further comprises at least one protruding ridge aligned longitudinal to the axis of said bottle holder located on said interior surface of said first section of said sleeve extending from said shoulder of said countercap to a predetermined point proximal to said first end of said countercap.

* * * * *